United States Patent [19]

Higaki et al.

[11] Patent Number: 4,504,423

[45] Date of Patent: Mar. 12, 1985

[54] PROCESS FOR PURIFYING DIBROMO-DICYANOBUTANE

[75] Inventors: Yoshikazu Higaki; Hiroyuki Omori, both of Mie, Japan

[73] Assignee: Mitsubishi Yuka Fine Chemicals Co., Ltd., Tokyo, Japan

[21] Appl. No.: 568,793

[22] Filed: Jan. 6, 1984

[30] Foreign Application Priority Data

May 12, 1983 [JP] Japan ................................. 58-82924

[51] Int. Cl.$^3$ .......................................... C07C 121/20
[52] U.S. Cl. .................................................. 260/465.7
[58] Field of Search ...................................... 260/465.7

[56] References Cited

U.S. PATENT DOCUMENTS

| | | | |
|---|---|---|---|
| 3,190,909 | 6/1965 | Inaba et al. | 260/465.7 X |
| 3,644,380 | 2/1972 | Harmetz et al. | 260/465.7 X |
| 3,833,731 | 9/1974 | Grier et al. | 260/465.7 X |
| 3,873,597 | 3/1975 | Harmetz et al. | 260/465.7 |
| 3,877,922 | 4/1975 | Grier et al. | 71/64 |
| 3,877,927 | 4/1975 | Martin | 71/105 |
| 3,929,858 | 12/1975 | Swigert | 260/465.7 |
| 4,435,251 | 3/1984 | Takeda et al. | 260/465.8 R X |
| 4,442,122 | 4/1984 | Engelhart et al. | 260/465.7 X |
| 4,446,076 | 5/1984 | Angeles | 260/465.7 X |

*Primary Examiner*—Joseph Paul Brust
*Attorney, Agent, or Firm*—Oblon, Fisher, Spivak, McClelland & Maier

[57] ABSTRACT

Dibromo-dicyanobutane is purified by washing with an aqueous solution of a compound wherein a cationic component is an alkali metal, alkaline earth metal, or ammonium ion and an anionic component is an oxygen-containing anion. The process can prevent dibromo-dicyanobutane from coloration, an irritating odor, and caking.

5 Claims, No Drawings

PROCESS FOR PURIFYING DIBROMO-DICYANOBUTANE

FIELD OF THE INVENTION

The present invention relates to a process for purifying dibromo-dicyanobutane. The process of this invention prevents dibromo-dicyanobutane from coloration, an irritating odor and caking.

BACKGROUND OF THE INVENTION

Dibromo-dicyanobutane such as 1,2-dibromo-2,4-dicyanobutane, 1,2-dibromo-1,4-dicyanobutane or 2,3-dibromo-1,4-dicyanobutane is useful as an intermediate for agricultural chemicals and pharmaceuticals. Particularly, 1,2-dibromo-2,4-dicyanobutane is industrially used as an antiseptic agent and mildewprooring agent which are effective against miscellaneous microorganisms which putrefy aqueous paints, adhesives, latices, emulsions, joint cements, woods and the like, and lower their viscosity.

The dibromo-dicyanobutane is produced by brominating an olefinic cyano compound. For example, 1,2-dibromo-2,4-dicyanobutane is produced according to the process disclosed in U.S. Pat. Nos. 3,877,922, 3,873,597, 3,833,731 and 3,644,380. The representative process is as follows.

2-Methyleneglutaronitrile is reacted in an aqueous medium with bromine which is added dropwise. After completion of the reaction, excess bromine is decomposed and removed by adding sodium bisulfite or the like. The solid reaction product which separates out after cooling is washed with water repeatedly, and the solid product obtained by filtering is dried under a reduced pressure.

The product thus obtained is preferably used in the form of fine powders, which increases the drying effect. Therefore, the pulverization of the product is usually accomplished prior to drying bulk solids formed. However, in order to attempt the pulverization in the course of the solid formation, a process wherein after decomposing excess bromine, a surfactant is added to emulsify, followed by cooling, is proposed.

It has been found that when 1,2-dibromo-2,4-dicyanobutane fine powder which was sufficiently washed with water is dried using a drying apparatus made of SUS, the product after drying markedly colors in orange and has a very irritating odor. It has been also found that the colored product cakes and loses the fine powder form when stored in a container, a so-called "caking phenomenon" in the powder engineering. As a result, the SUS dryer used was corroded so severely that could not be further used.

The above problems deteriorate the quality of dibromo-dicyanobutane as the product in the various field of use thereof, resulting in remarkably decreasing the commercial value. The caking of the product requires to crush and pulverize the bulk product prior to withdrawing from a container or adding to a desired product, making the operation complicated. Further, the irritating odor is not preferred to operators from the hygienic standpoint.

To overcome those problems, the colored product was washed with water repeatedly, but the coloration did not disappear and the irritating odor did not lose. The problems may be overcome to some extent if the drying temperature is lowered and a dryer made of glass is used. Further, recrystallization using an organic solvent such as isopropanol may be of some help to overcome the problems.

However, the above proposals are difficult to sufficiently overcome the problems and are not industrially preferred manners in increasing a number of steps, cost for equipment, cost for workers and the like.

SUMMARY OF THE INVENTION

As the result of extensive studies, it has been found that the above disadvantageous problem can be overcome by washing treatment of dibromo-dicyanobutane with water and then washing treatment of the same with an aqueous solution of a specific inorganic salt.

Accordingly, an object of this invention is to provide a process for purifying a dibromo-dicyanobutane which comprises washing the dibromo-dicyanobutane with an aqueous solution of a compound in which the cationic component is an alkali metal, alkaline earth metal, or ammonium ion, and the anionic component is an oxygen-containing anion.

DETAILED DESCRIPTION OF THE INVENTION

The compound used as an aqueous solution in the process of this invention is a compound wherein a cationic component is an alkali metal, alkaline earth metal or ammonium ion, and an anionic component is an oxygen-containing anion. Examples of such compounds include nitrate, sulfate, phosphate, formate and carbonate of the cation component.

Of the cation components, the alkali metal and ammonium ion are preferred, and sodium ion, potassium ion and ammonium ion are particularly preferred. Of the anion components, a nitrate radical and sulfate radical are preferred, and the nitrate radical is particularly preferred.

According to the process of this invention, dibromo-dicyanobutane is treated with an aqueous solution of the above-mentioned compound. The treatment temperature is 0° to 70° C., preferably 10° to 40° C. The concentration of the aqueous solution is 0.01 to 5.0 wt%, preferably 0.1 to 5.0 wt%. The amount of the aqueous solution for the dibromo-dicyanobutane is such that the concentration of dibromo-dicyanobutane in the aqueous solution is 0.01 to 200 wt%, preferably 1 to 100 wt%, but the amount is not particularly limited.

Dibromo-dicyanobutane is obtained by, for example, brominating 2-methyleneglutaronitrile, cooling the reaction mixture to precipitate a solid product and separating the solid product by filtration. The reaction solid product thus obtained can be directly washed with water and then treated with an aqueous solution of the above-mentioned compound according to the process of this invention.

The invention is now described in more detail by reference to the following examples and comparative examples.

The term "Value of Caking Tendency" used in the examples denotes quantitatively the degree of caking that takes place when powder is stored. It is measured according to the method described in *Industrial and Engineering Chemistry*, Vol. 33, No. 1, p. 121 (1941). According to this method, a sample is caused to cake intentionally using a pressurizing apparatus and the force required to break the caked material is measured.

COMPARATIVE EXAMPLE 1

Into a 1 liter four-neck flask equipped with a thermometer, stirrer, reflux condenser and dropping funnel were charged 63.0 g of 2-methyleneglutaronitrile (purity 99.8%) and 350 g of water. When the contents in the flask were heated to 40° C., 95.2 g of bromine was added dropwise from the dropping funnel over about 2 hours. During the dropwise addition, heating was continued and when the addition was completed, the temperature was 60° C. Reaction was further continued at 80° C. for 1 hour to age. After cooling to 75° C., sodium bisulfite was added to reduce excess bromine into hydrogen bromide. An emulsifier was then added to emulsify the reaction product. The emulsion was cooled at a rate of 1° to 2° C./hour to give crystals of 1,2-dibromo-2,4-dicyanobutane. The crystals were filtered out and washed thoroughly with water until the emulsifier and sodium bisulfite were not detected any longer. Thus, 172 g of 1,2-dibromo-2,4-dicyanobutane containing water was obtained. The solid product was dried under a reduced pressure. To observe the corrosive effect on SUS, a test piece (2.0×3.0×0.2 cm) made of SUS-304 was placed together with 1,2-dibromo-2,4-dicyanobutane in a vacuum drier made of glass. Drying was performed under a reduced pressure of 10 to 25 mmHg at 40° C. for 0.5 hour. The water content was 300 ppm or less.

The dried 1,2-dibromo-2,4-dicyanobutane colored in orange remarkably and had a strong irritating odor. The melting point thereof was 51.0° to 52.0° C. In view of the fact that a product obtained by recrystallization from isopropanol had a melting point of 51.1 to 51.8° C., the colored product was substantially equal in purity to the recrystallized product.

Next, the degree of coloration of the colored product was measured.

1.0 g of the colored product was dissolved in 10 g of acetone. The absorbance of the solution at 420 nm was 0.339.

1.0 g of the colored product was placed in a cylinder made of SUS, having a depth of 2 cm and a cross-sectional area of 0.785 cm$^2$ and compressed at 20° C. for 24 hours under a pressure of 7736 g/cm$^2$ to accelerate caking. The pressure G which breaks the 10 mm diameter cylindrical product of the caked solid product was measured. The G valve was 1,000 g/cm$^2$. This indicated that the solid product was very easy to cake.

EXAMPLE 1

The reaction product obtained in the same manner as in Comparative Example 1 was filtered and sufficiently washed with water. The product was then washed in 782 g of 1% aqueous solution of sodium nitrate (the concentration of 1,2-dibromo-2,4-dicyanobutane: 22 wt%) while stirring for about 2 to 3 minutes and filtered off. The resulting water-containing solid product was dried under a reduced pressured in the same manner as in Comparative Example 1 until the water content became 300 ppm or less.

The dried solid product had a melting point of 51.0° to 52.0° C., showed a complete white color and did not have an irritating odor. In addition, corrosion of the test piece was not observed. The acetone solution of the solid product gave an absorbance of 0.0141. The G value showing the value of caking tendency was 25 g/cm$^2$. This indicated that the product was extremely difficult to cake.

EXAMPLES 2 to 12 and COMPARATIVE EXAMPLES 2 to 8

Treatment of 1,2-dibromo-2,4-dicyanobutane was carried out in the same manner as in Comparative Example 1 except that the washing manner and the drying temperature were changed as shown in Table 1. The results are shown in Table 1.

TABLE 1

| | Washing Manner | Drying temperature (°C.) | Test piece | Degree of coloration | Value of caking tendency (g/cm$^2$) | Odor | Corrosion of test piece |
|---|---|---|---|---|---|---|---|
| Comparative Example No. | | | | | | | |
| 1 | Water washing | 0 | SUS-304 | 0.035 | — | Weak irritating odor | Slight |
| 2 | Water washing | 30 | SUS-304 | 0.050 | — | Irritating odor | Severe |
| 3 | Water washing | 40 | SUS-304 | 0.339 | 1000 | Strong irritating odor | Severe |
| 4 | Water washing | 30 | — | 0.02 | 160 | Irritating odor | — |
| 5 | After water washing recrystallizing from isopropanol | 40 | — | — | 400 | No odor | — |
| 6 | Water washing | 40 | *2 | 1.825 | — | Strong irritating odor | Severe |
| 7 | *1 | 40 | SUS-304 | 0.130 | — | Irritating odor | Severe |
| 8 | Water washing + treatment with 1% NaCl aq. soln. | 40 | SUS-304 | 0.128 | — | Strong irritating odor | Severe |
| Example No. | | | | | | | |
| 1 | Water washing + treatment with 1% NaNO$_3$ aq. soln. | 40 | SUS-304 | 0.014 | 25 | No odor | None |
| 2 | Water washing + treatment with 1% KNO$_3$ aq. soln. | 40 | SUS-304 | 0.011 | — | No odor | None |
| 3 | Water washing + treatment with 1% Al(NO$_3$)$_3$ aq. soln. | 40 | SUS-304 | 0.014 | — | No odor | None |
| 4 | Water washing + treatment with 1% NaSO$_4$ aq. soln. | 40 | SUS-304 | 0.008 | 195 | Weak irritating odor | None-slight |
| 5 | Water washing + treatment with 1% Na$_2$C$_2$O$_4$ aq. soln. | 40 | SUS-304 | 0.005 | — | No odor | Severe |
| 6 | Water washing + treatment | 40 | SUS-304 | 0.068 | — | Weak irritating odor | Slight |

TABLE 1-continued

|   | Washing Manner | Drying temperature (°C.) | Test piece | Degree of coloration | Value of caking tendency (g/cm²) | Odor | Corrosion of test piece |
|---|---|---|---|---|---|---|---|
| 7 | with 1% Na₂CO₃ aq. soln. water washing + treatment with 1% NH₄NO₃ aq. soln. | 40 | SUS-304 | 0.012 | 500 | No odor | None |
| 8 | Water washing + treatment with 1% Na₃PO₄ aq. soln. | 40 | SUS-304 | 0.041 | — | Irritating odor | Slight |
| 9 | Water washing + treatment with 1% NaNO₂ aq. soln. | 40 | SUS-304 | 0.046 | 530 | No odor | None |
| 10 | Water washing + treatment with 1% KiO₂ aq. soln. | 40 | SUS-304 | 0.098 | 420 | Weak irritating odor | Slight |
| 11 | Water washing + treatment with 1% NaClO₄ aq. soln. | 40 | SUS-304 | 0.022 | 340 | Weak irritating odor | Severe |
| 12 | Water washing + treatment with 1% NaSO₃ aq. soln. | 40 | SUS-304 | 0.029 | — | Irritating odor | Slight-Severe |

Notes
*1 Water washing the colored product obtained in comparative Example 3 + treatment with 1% NaNO₃ aqueous solution.
*2 SUS-304 treated with 10% nitric acid.

As is apparent from the above results, the process of this invention can prevent the coloration and odor of dibromo-dicyanobutane and also the corrosion of production apparatus and can further prevent the physical phenomenon of "Caking Phenomenon" of a powdery solid.

While the invention has been described in detail and with reference to specific embodiments thereof, it will be apparent to one skilled in the art that various changes and modifications can be made therein without departing from the spirit and scope thereof.

What is claimed is:

1. A process for purifying dibromo-dicyanobutane which comprises washing dibromo-dicyanobutane with an aqueous solution of a compound in which the cationic component is an alkali metal, alkaline earth metal or ammonium ion, and the anionic component is an oxygen-containing anion selected from the group consisting of nitrate, sulfate, phosphate, formate and carbonate.

2. A process as claimed in claim 1, wherein the cation component is selected from the group consisting of sodium ion, potassium ion and ammonium ion.

3. A process as claimed in claim 1, wherein the anion component is selected from the group consisting of nitrate and sulfate.

4. A process as claimed in claim 1, wherein the compound is selected from the group consisting of sodium nitrate, potassium nitrate, ammonium nitrate, sodium sulfate, potassium sulfate and ammonium sulfate.

5. A process as claimed in claim 4, wherein the compound is selected from the group consisting of sodium nitrate, potassium nitrate, ammonium nitrate and sodium sulfate.

* * * * *